United States Patent [19]

Harandi et al.

[11] Patent Number: 4,877,921

[45] Date of Patent: Oct. 31, 1989

[54] SINGLE ZONE OLIGOMERIZATION OF OLEFINS IN A SUPER-DENSE PHASE TURBULENT FLUID BED

[76] Inventors: Mohsen N. Harandi, 12 Catbird Ct., Lawrenceville, N.J. 08648; Hartley Owen, 5 Riverview Ter., Belle Mead, N.J. 08502

[21] Appl. No.: 184,465

[22] Filed: Apr. 20, 1988

[51] Int. Cl.$^4$ ............................ C07C 3/10; C07C 3/20
[52] U.S. Cl. ..................................... 585/533; 585/739
[58] Field of Search ............... 585/734, 739, 533, 531; 208/113, 120

[56] References Cited

U.S. PATENT DOCUMENTS

| | | | |
|---|---|---|---|
| 4,150,062 | 4/1979 | Garwood, et al. | 260/673 |
| 4,417,086 | 11/1983 | Miller | 585/533 |
| 4,417,087 | 11/1983 | Miller | 585/530 |
| 4,417,088 | 11/1983 | Miller | 585/533 |
| 4,423,269 | 12/1983 | Miller | 585/533 |
| 4,430,516 | 2/1984 | La Pierre, et al. | 585/533 |
| 4,547,609 | 10/1985 | Dessau | 585/517 |
| 4,547,613 | 10/1985 | Garwood et al. | 585/533 |
| 4,666,998 | 5/1987 | Hagerty | 526/68 |
| 4,746,762 | 5/1988 | Aridan et al. | 585/533 |

OTHER PUBLICATIONS

Arthur M. Squires, et al./Fluid Beds: At Last, Challenging Two Entrenched Practicies/Dec. 20, 1985, vol. 230, pp. 1329–1337.

*Primary Examiner*—Glenn Caldarola
*Attorney, Agent, or Firm*—Alexander J. McKillop; Charles J. Speciale; Lowell G. Wise

[57] ABSTRACT

A turbulent super-dense fluid-bed of a medium pore zeolite metallosilicate catalyst is operated at low WHSV, outside a critical region in the phase diagram of the hydrocarbon mixture in the reactor, at or above conditions of pressure $P_{max}$ and temperature $T_{max}$ at which a liquid phase may not form. The result is oligomerization of a "light gas" predominantly $C_3$–$C_5$ olefin feed, the remainder being mainly $C_3$–$C_5$ lower alkanes. The oligomerized product is a "heavies" stream, namely, distillate and lube oil range hydrocarbons, with a minor proportion by weight of gasoline range hydrocarbons. The reactor may be operated in either a $C_1^+$ distillate mode, or, a $C_{22}^+$ lubes mode. The superdense fluid bed with a density, measured at the bottom of the reaction zone, greater than 500 kg/m$^3$, and operates at a temperature in the range from about 204° C. (400° F.) to about 371° C. (700° F.), and a pressure in the range from about 2857 kPa (400 psig) to about 13880 kPa (2000 psig) or even higher. This unique process provides per pass conversion of olefins, and selectively to $C_5^+$ hydrocarbons, each in excess of 80%.

22 Claims, 2 Drawing Sheets

SINGLE ZONE OLIGOMERIZATION OF OLEFINS IN A SUPER-DENSE PHASE TURBULENT FLUID BED

BACKGROUND OF THE INVENTION

This invention relates to a fluid-bed catalytic process for upgrading olefinic light gas feedstock (termed "light gas" for brevity herein) containing lower, particularly $C_3$–$C_5$, olefins (alkenes) and paraffins (alkanes). The olefins are converted to heavier hydrocarbons ("heavies") in a single-zone fluid-bed reactor, operating at pressure and temperature conditions at which it is critical that there be no liquid phase present. These operating conditions are referred to herein as $P_{max}$ and $T_{max}$. Such conditions prevail at near-critical and super-critical pressure and/or temperature in a super-dense phase turbulent regime. By "near-critical" we refer to a pressure of at least 2857 kPa (400 psig), and a temperature of at least 204° C. (400° F.) which is always above the critical temperature of the feed. In other words, the reactor converts light gas to heavies in a single zone of turbulent regime, operating at a pressure and temperature outside a tightly circumscribed region of pressure and temperature ("critical P & T region") which region lies near, or above the apex of a phase diagram defining the critical point ($P_{cr}$, $T_{cr}$) of the mixture of hydrocarbons in the reactor. We know of no other process which can convert olefins to distillate or lube oil in high yield, in a single zone.

Moreover, we accomplish this with an unexpected degree of flexibility. The operating pressure and temperature conditions may be supercritical (that is, both are above $P_{cr}$, $T_{cr}$ of the mixture); or, only one or the other may be below $P_{cr}$, $T_{cr}$; or, both may be below $P_{cr}$, $T_{cr}$; provided they are not in the critical P & T region so that no liquid can form. Operation at precisely $P_{cr}$, $T_{cr}$ conditions, or too close to them (within the critical P & T region), involves too high a risk of formation of a liquid phase, and is therefore avoided. At, or above $P_{max}$ and $T_{max}$, under near-critical or super-critical conditions, the entire bed is in a fluid phase in which the solid acts as catalyst and heat transfer sink. In this process, we regard the super-dense phase as being neither gas nor liquid, but for convenience and familiarity, we treat the oligomerization reaction as being a gas/gas reaction.

More particularly, the invention provides a continuous process for oligomerizing light gas containing propene, butenes and pentenes, preferably in the absence of added hydrogen, to a $C_{10}^+$ rich hydrocarbon stream, in either of two operating modes. In one mode the reactor is operated at relatively low pressure in the range from about 2857 kPa to about 10436 kPa (400 psig–1500 psig), and relatively high temperature in the range from 260° C. to about 371° C. (500° F. –700° F.), referred to as the "distillate mode"; in the other mode the reactor is operated at relatively high pressure in the range from about 5270 kPa to about 13881 kPa (500 psig–2000 psig), and relatively low temperature in the range from 204 C. to about 315° C. (400° F.–600° F.), referred to as the "lubes mode". Even higher pressures, as high as 20821 kPa (3000 psig) may be used if the economics of operating at such high pressure can be justified by the lube "make". By "distillate" we refer to $C_{10}^+$ hydrocarbons boiling in the range from about 138° C. to about 349° C. (280° F.–660° F.); by "lubes" we refer to high-boiling hydrocarbons having a viscosity in the range from 10 cp to about 100 cp, measured at 100° C. The particular operational mode chosen depends upon which particular boiling range of oligomerized product is desired, though in either case a minor amount of $C_5^+$ gasoline range hydrocarbons may also be formed. When this occurs, the gasoline, typically not a desired product in our process, is recycled to yield the desired distillate or lubes product. Light gas containing a substantial, preferably a major portion, typically more than 75% of combined propene and butenes, is a particularly well-suited feed to the reactor.

Developments in fluid-bed catalytic processes using a wide variety of zeolite catalysts have spurred interest in commercializing the conversion of olefinic feedstocks for producing $C_5^{30}$ gasoline, diesel fuel, etc. In addition to the discovery that the intrinsic oligomerization reactions are promoted by ZSM-5 type zeolite catalysts, several discoveries relating to implementing the reactions in an apt reactor environment, have contributed to the commercial success of current industrial processes. These are environmentally acceptable processes for utilizing feedstocks that contain lower olefins, especially $C_3$–$C_5$ alkenes, though some ethene (ethylene), and some olefins and paraffins heavier than $C_5$ may also be present.

Of particular interest is that the ZSM-5 type catalyst used under our severe process conditions does not appear to suffer from a sensitivity (poisoning) to basic nitrogen-containing organic compounds such as alkylamines ( e.g. diethylamine), or, to oxygenated compounds such as ketones, a proclivity which is characteristic of the catalyst under the process conditions of prior art olefin oligomerization processes. Such processes require the addition of hydrogen as a preventative antidote. It will be recognized that alkylamines are used in treating light gas streams, and ketones are typically present in Fischer Tropsch-derived light ends streams, both of which streams are particularly well-suited for upgrading by oligomerization. Though our process is not adversely affected by the presence of hydrogen, there is no readily discernible economic incentive for using it in our single stage reactor, and we prefer not to do so.

Conversion of $C_3$–$C_5$ alkenes and alkanes to produce aromatics-rich liquid hydrocarbon products were found by Cattanach (U.S. Pat. No. 3,760,024) and Yan et al (U.S. Pat. No. 3,845,150) to be effective processes using the ZSM-5 type zeolite catalysts. In U.S. Pat. Nos. 3,960,978 and 4,021,502, Plank, Rosinski and Givens disclose conversion of $C_2$–$C_5$ olefins, alone or in admixture with paraffinic components, into higher hydrocarbons over crystalline zeolites having controlled acidity. Garwood et al have also contributed to the understanding of catalytic olefin upgrading techniques and have contributed improved processes as in U.S. Pat. Nos. 4,150,062, 4,211,640 and 4,227,992. The '062 patent discloses conversion of olefins to gasoline or distillate in the range from 190°–315° C. and 42–70 atm; and this, and the '640 and '992 disclosures are incorporated by reference thereto as if fully set forth herein.

The prior art processes relate to the conversion of lower olefins, especially propene and butenes, over ZSM-5 and HZSM-5, at moderately elevated temperatures and pressures. The sought-after conversion products are liquid fuels, especially the $C_6^{30}$ aliphatic and aromatic hydrocarbons. It is known that the product distribution may be tailored by controlling process conditions, such as temperature, pressure and space velocity. Gasoline ($C_{6-10}$) is readily formed at elevated temperature (preferably about 400° C.) and pressure from ambient to about 2900 kPa (420 psia), preferably about 250 to 1450 kPa (36 to 210 psia). Olefinic gasoline can be produced in good yield and may be recovered as a product or fed to a low severity, high pressure reactor system for further conversion to heavier distillate-range products. Distillate mode operation can be employed to maximize production of $C_{10}{}^+$ aliphatics by reacting the lower and intermediate olefins at high pressure and moderate temperature. Operating details for typical "MOGD" (for Mobil Olefin to Gasoline & Distillate) oligomerization units are disclosed in U.S. Pat. Nos. 4,456,779 and 4,497,968 (Owen et al); 4,433,185 (Tabak); and Ser. No. 006,407 (Avidan et al) filed Jan. 23, 1987 issued as U.S. Pat. No. 4,746,762. Because our process is preferably operated for the production of distillate and lubes it is referred to as the "MODL" (for Mobil Olefin to Distillate & Lubes) process.

Lower olefin feedstocks containing $C_2-C_6$ alkenes may be converted selectively either to a higher or lower boiling range product by varying pressure, temperature, the type of catalyst, and the mass flow through the reactor. Despite the very high-pressure and temperature used in the reaction of our process, the difficulty of converting ethene is not overcome, and, unlike the foregoing '407 Avidan et al process, our process is not particularly directed to the conversion of a major amount of ethene, if it is present in the feed. However our process may oligomerize a good portion of ethene. It is well known that ethene conversion increases as temperature increases in the range from about 204° C. to 316° C. (400°-600° F.), but the strictures of operation in the prior art fluid-bed processes demand a catalyst cycle time which does not permit good conversion in this temperature range at conventional fluid-bed pressures. Because our process, in its high temperature mode, can operate continuously at the high end of the foregoing temperature range at near-critical or super-critical pressures, it favors oligomerization of ethene, but because of the higher pressure and bed density than in the Avidan '407 process, oligomerization of higher alkenes than ethene is far more highly favored.

To date, in a refinery for crude petroleum, very high pressure reactors (at least 400 psig) in which there is a deliberate effort made to provide a thoroughly mixed catalyst in the fluid phase, was limited to the multiphase contacting of liquid-solids-gas systems, such as in the hydrogenation of liquids in the presence of catalyst, as for example in the hydrogenation of heavy residuum hydrocarbons for the purposes of hydrodesulfurization, hydrocracking or similar processes, exemplified by that disclosed in U.S. Pat. No. 3,363,992 to Chervenak.

We have now found that $C_3-C_4$-rich and higher olefins may be selectively upgraded to normally liquid hydrocarbons in either the distillate or lubes ranges by catalytic conversion in a turbulent fluidized bed of solid acid zeolite catalyst with an alpha (activity) in a broad range from about 2 to 100, operating at or above $P_{max}$ and $T_{max}$, in the super-dense phase, in the absence of added hydrogen, in a single pass, or with recycle of undesired oligomerized product.

However, the most important advantage is the close temperature control afforded by operation of a fluid-bed in the turbulent regime (referred to as a "turbulent bed"). An essentially uniform conversion temperature may be maintained (often with closer than ±5° C. tolerance). Except for a small zone adjacent the bottom gas inlet, the midpoint measurement is representative of the entire bed, due to the thorough mixing achieved. Nothing in the prior art teaches how to operate a super-dense phase fluid-bed in the turbulent regime, or what the effects of doing so might be. Nor is there any suggestion as to how to predict the minimum and complete fluidization velocities, $U_{mf}$ and $U_{cf}$ respectively, or the minimum bubbling velocity $U_{mb}$, at or above $P_{max}$ and $T_{max}$.

The foregoing notwithstanding, the simple fact was that at a pressure sufficiently high to produce a super-dense phase in the bed, it was unlikely that there would be the requisite amount of backmixing deemed an essential characteristic of a turbulent bed of an aeratable (group A) powder. Much backmixing of gas in the dense phase occurs, and gas exchange between bubbles and the dense phase is high, due to splitting and recoalescence, which is why the turbulent regime in a dense phase bubbling bed provides a region of backmixing (see E. R. Gilliland and E. A. Mason, *Ind. Eng. Chem.*, 41, 1191, 1949). In a super-dense phase bed, there is no experimental evidence to expect that bubbles would drag solids upwards, and that a backflow of solids elsewhere would carry interstitial gas downward. Since, at very high pressure, the bubbles are not only minute, but have minimal vertical movement, it appeared most unlikely that operation at near-critical or super-critical pressure would provide the necessary backmixing.

Moreover, in turbulent beds, fluidization is better at a higher fluidizing gas velocity, and with a higher level of the finer sizes of catalyst (see R. M. Braca and A. A. Fried, in *Fluidization*, D. F. Othmer, Ed. (Reinhold, New York, 1956), pp. 117-138; W. W. Kraft, W. Ulrich, W. O'Connor, ibid., pp. 184-211). This requires a significant amount of fines, from about 10 to 25 % by weight (% by weight) having a particle size less than 32 microns. In a super-dense, turbulent bed, how and why would one expect to confine such a relatively large amount of fines, assuming they were desirable, if not essential, for the operation of the bed?

U.S. Pat. Nos. 4,417,086 and 4,417,087 to Miller teach a two-zone reactor operating in the transport mode where the relative superficial gas velocity is greater than the terminal velocity in free fall. Though the operation of a fluid-bed is illustrated (example 2 in each of the '086 and '087 patents) note that no operating pressure is state din the former, and that operating pressure in the latter is 10 psig (24.7 psia, 170 kPa). The general disclosure that the processes may be operated at a pressure in the range from subatmospheric to several hundred atmospheres, but preferably 10 bar or less, and most preferably 0 to 6 bar, (see middle of col 6 in '086, and, near top of col 5 in '087) is not so ingenuous as to be meant to apply equally to the fixed bed (example 1 of '086 and '087, each illustrates 34.5 bar, 500 psi) and the 170 kPa fluid-bed.

Another incidental disclosure of operation of a fixed bed of a zeolite, particularly a large pore zeolite having pore dimensions greater than about 6 A (angstroms), at high pressure, up to 13,780 kPa (2000 psig) and temperature, up to 399° C. (750° F.) for the catalytic conversion of olefins to heavies, is found in U.S. Pat. No. 4,430,516 to Pierre et al. But they did not state the obvious, namely, that the conditions they specified, applied to a fixed bed reactor; nor could they have, because at that time, a fluid-bed in a dense phase turbulent regime, let alone a superdense one at near-critical or super-critical conditions, had simply never been considered, let alone operated.

Moreover, if denser fluidization regimes are viewed as comprising systems in which transient clusters of relatively large, dense aggregates of particles are dispersed in a dilute continuum of sparsely distributed, smaller clusters, how would a superdense regime be viewed? How applicable would the empirical Richardson-Zaki equation (see J. F. Richardson, and W. F. Zaki, *Trans. Inst. Chem. Eng.* 32, 35, 1954) be under near-critical or supercritical conditions? Finally, apart from the mechanics of operating the super-dense fluid-bed, how would the catalytic activity of porous crystalline aluminasilicate catalysts, (group A powders, see A. M. Squires, M. Kwauk and A. A. Avidan *Science*, 230, 1329-1337, 1985) be affected by conditions in the superdense bed? Since fluid-beds are more competitive in larger sizes, and scale-up of group A fluid-beds is notoriously difficult when high conversions of reactants are desired, how would one expect to provide an operable super-dense fluid-bed? How would one expect to cope with the reality that near-critical and super-critical conditions for the product would be quite different from those for the light gas feed, or recognize the significance of the difference?

Thus to date, a high pressure zeolite fluid-bed process was limited to a pressure of 2500 kPa (363 psia). For example, in the '407 Avidan process, the ethene-containing C+olefinic feedstock is converted in a catalytic reactor operating under elevated pressure (410 to 2500 kPa) and temperature (315 to 510° C.) to convert at least 70% of feedstock ethene in the light gas into $C_8$ + hydrocarbons rich in gasoline-range olefins and aromatics. But the process conditions of our invention are substantially different from those for the '407 process, and though our process favors conversion of some ethene, as will be explained hereinafter, our process is not directed to the conversion of a major proportion of ethene, yet is quite suddenly highly effective with $C_3=+$ olefins.

SUMMARY OF THE INVENTION

It has been discovered that a turbulent super-dense fluid-bed of a medium pore zeolite metallosilicate catalyst may be operated at low WHSV (it being understood that WHSV signifies pounds of feed per pound of zeolite per hour), at or above conditions of pressure and temperature (at or above $P_{max}$ and $T_{max}$) at which a liquid phase may not be present, so as to oligomerize a "light gas" feed containing $C_2$-$C_6$, but predominantly $C_3$-$C_5$ olefins (the remainder substantially being $C_3$-$C_5$ lower alkanes) to "heavies", namely, distillate and lube oil range hydrocarbons, and recycling such gasoline components as may be formed, to produce a substantially "heavies" product stream.

More specifically, to produce desirable oligomerized product effectively, it has been discovered that the super-dense phase fluid bed (referred to hereinabove) is required to be operated at or above $P_{max}$ and $T_{max}$ of either the hydrocarbon feed, the effluent oligomerized product, or any intermediate hydrocarbon formed during the reaction; in other words, operation requires that the pressure and temperature be maintained outside a critical region (critical P & T region) in the phase diagrams of either the feed, the product, or any intermediate. This critical P & T region is defined by an arc circumscribed around the critical point, between the vertical through the critical point, and, the dew point curve of the phase diagram, the arc having a radius corresponding to about 344.5 kPa (50 psia).

It is therefore a general object to provide a process for oligomerizing an olefin-containing feedstream consisting essentially of "light gas" containing (ethene and heavier), but +hydropredominantly $C_3$+ olefins, to a "heavies" product ($C_{10}$+ carbons), comprising, operating a super-dense phase fluid-bed in the turbulent regime at or above $P_{max}$ and $T_{max}$ outside the abovedefined critical region in the phase diagram of the hydrocarbon mixture in the bed, while flowing a light gas feed through the bed which consists essentially of a finely divided medium pore zeolite metallosilicate catalyst having a constraint index in the range from 1 to 12, and a fresh catalyst activity (alpha) in the range from about 50 to 100; and, to provide a high pressure MODL reactor which in combination with a regenerator, is particularly adapted to carry out the foregoing process.

It is a more specific object of this invention to provide a catalytic process for upgrading light gas feed to heavier product rich in $C_{10}$+ aliphatic hyrocarbons, the process comprising, (a) contacting said light gas with a finely divided porous aluminosilicate catalyst having a constraint index in the range from about 5 to about 12, an operating alpha preferably in the range from about 2 to 25, and most preferably from about 5 to about 15, maintained as a super-dense fluid-bed operating in a single zone turbulent regime at or above $P_{max}$ and $T_{max}$, without requiring the addition of hydrogen to counteract poisoning of the catalyst, (b) flowing said light gas through said bed at a weight hourly space velocity (WHSV) in the range from about 0.05 to about 50 $hr^{-1}$, and preferably from 0.1 to 10 $hr^{-1}$ without forming a liquid phase in said bed, (c) maintaining a content of catalyst fines in the range from about 5% to about 20% by wt, based on the weight of the catalyst in the bed, said fines having a particle size less than 32 microns, and, (d) recovering said heavies from a product stream leaving in the near-critical or super-critical fluid phase from said bed.

More specifically, it has been found that the conversion of light gas having an olefinic content of at least 20% by wt of propylene, or heavier light olefins ($C_4=+$), may be tailored to produce either $C_{10}$+ distillate, or 10-100 cp viscosity (100° C.) lubes, under elevated pressure and temperature conditions above $P_{max}$ and $T_{max}$, the higher the pressure, the lower the temperature required to produce heavier heavies:

(i) most preferably beginning at about 2857 kPa (400 psig) and about 315° C. (600° F.), up to about 6890 kPa (1000 psig) and 288° C. (550° F.) to produce distillate; and, (ii) beginning at about 8714 kPa (1250 psig) and about 260° C. (500° F.), up to about 11125 kPa (1600 psig) and 232° C. (450° F.) to produce lubes, respectively;

and, the overall yield ("make") of each of the foregoing products may be optimized by recycling an insufficiently oligomerized portion of the product stream to the reactor.

Specifically, the "make" of the process is sensitive to operating pressure at or above $P_{max}$ and $T_{max}$ within the broad range of from about 2857 kPa to about 13880 kPa (400-2000 psig), and particularly in the high pressure mode from 5200 to 13880 kPa (750-2000 psig). Preferred operation excludes a region circumscribed by about a 50 psia differential from $P_{cr}$, $T_{cr}$ of the hydrocarbon mixture in the bed, and bounded by the portion of the bubble-point/dew-point curve downwardly inclined from said point. Under such high pressure conditions, the reaction is prejudiced in favor of oligomerization with a minimum of cracking of alkanes, so that particular ranges of temperatures are found most desirable for a "make" in a specific hydrocarbon boiling range (gasoline, distillate or lubes). The precise optimum combination of pressure and temperatures, along with WHSV, for a particular catalyst, is best arrived at with such trial and error as one skilled in the art is enured to.

BRIEF DESCRIPTION OF THE DRAWINGS

The foregoing and other objects and advantages of our invention will appear more fully from the following description, made in connection with the accompanying drawings of a preferred embodiment of the invention, wherein.

DETAILED DESCRIPTION OF PREFERRED EMBODIMENTS

When a vapor at a given pressure is cooled, liquid just commences to form at the temperature for which that pressure is the saturation value; this principle is utilized in the dew-point method for determining vapor pressures of a typical light gas to be converted into a 'heavies' product for which the dew-point is similarly determined. Dew-point is defined as the temperature at which condensation of the vapor in the atmosphere takes place.

Figure 1:
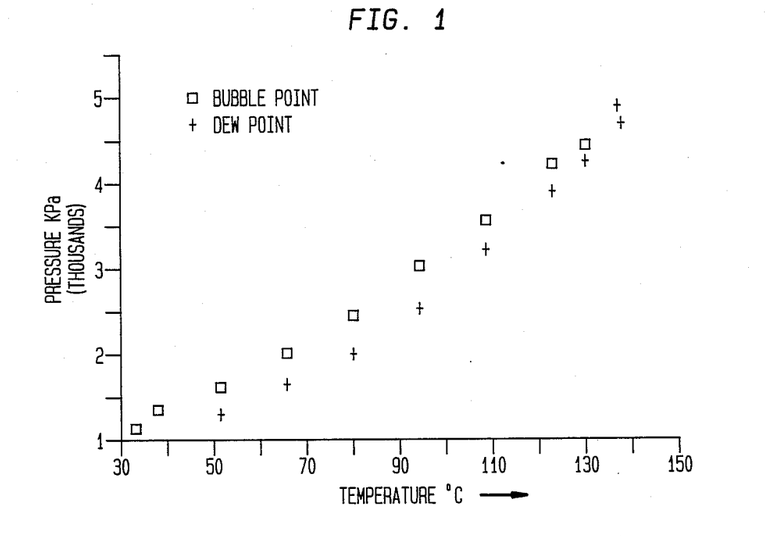
FIG. 1 is a phase diagram showing a plot of dew-point and bubble-point curves for a typical light gas.

Referring now to FIG. 1 there is shown a plot of dew-point and bubble point curves in a phase diagram for temperatures ranging from about 37.8° C. (100° F.) and about 689 kPa (100 psia), to the critical point, about 132° C. (270° F.) and 4272 kPa (620 psia), of a typical light gas feed having the following composition:

| | |
|---|---|
| $C_3^=$ | 25.5% by wt. |
| $C_3$ | 7.6% |
| $C_4^=$ | 43.7% |
| $C_4$ | 23.14% |

It is evident from the phase diagram for the feed, that above about 965 kPa (140 psia) there is less than about 23° C. (50° F.) separating the gas and liquid phases. The difference in temperature becomes progressively smaller as the pressure increases, becoming zero at the critical point.

Since it is essential that the process operates in the super-dense turbulent phase without the formation of liquid, it is critical that the dew-point curve never be traversed. In other words, P & T conditions for operation of the process must ensure that no liquid will be formed, whether from the feed, the product, or the intermediates formed during the reaction. Such conditions obtain at near-critical or super-critical conditions.

Figure 2:
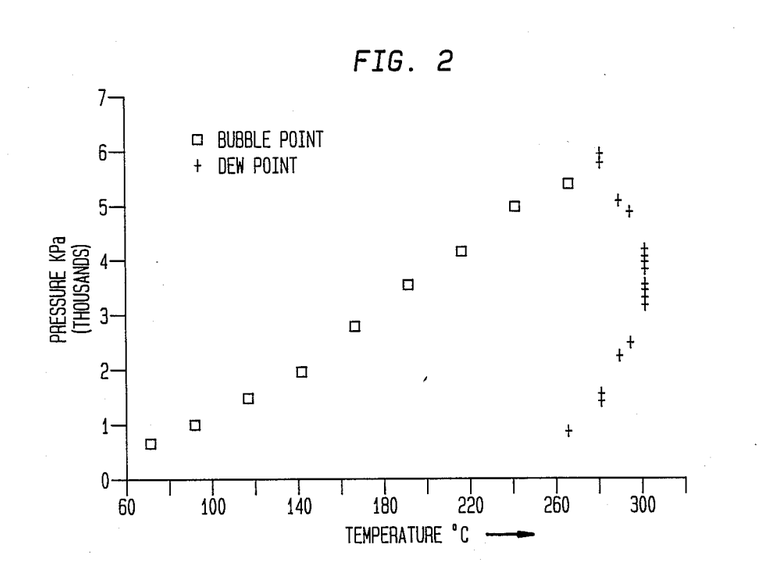
FIG. 2 is a phase diagram showing a plot of dew-point and bubble-point curves for a typical gasoline range hydrocarbon product produced in our process.

With the particular feed characterized by the phase diagram given in FIG. 1, the reactor may be operated in a distillate mode to produce a distillate characterized by the phase diagram shown in FIG. 2. For such operation, by "near-critical" we refer to a pressure which may be more than 2412 kPa (350 psia), but not less than about 344.5 kPa (50 psia), below the critical pressure $P_{cr}$, so long as the temperature is above $T_{max}$, the temperature at, or above which no liquid may be present. As will be seen by reference to FIG. 2, the more the lower portion of the bubble point curves inwards from the vertical, the lower the pressure at which one can operate at or above $T_{max}$. In other words, the MODL reactor can operate at a relatively low pressure outside the critical P & T region (defined hereinabove). In operation with light gas, the operating pressure is preferably at least 2857 kPa (400 psig), and $T_{max}$ is about 265° C.) (510° F.), though the reactor may be operated at as low a pressure as 2857 kPa (400 psig).

By "super-critical" conditions we refer to conditions above $P_{cr}$, $T_{cr}$ for the product, and outside the "envelope" of the phase diagram. Since operating conditions of the fluid bed are chosen so that no liquid is formed during the reaction, it is essential that not only the more expanded phase envelope (compared to the relatively narrow one for the feed) for the product be considered, but also all phase envelopes for the hydrocarbon intermediates formed during the reaction. The product contains heavier molecules made during the reaction, so that the phase envelope for the product is distinguishable over that for the feed in that the former is now relatively expanded, and shifted towards higher temperatures. When the desired product selectivity is obtained at a temperature above that corresponding to the dew-point curve of the product, and above at least 204° C. (400° F.), the optimum (low) pressure may be used to minimize equipment cost. If the desired selectivity cannot be obtained at $T_{max}$, or a temperature just above it, then the operating pressure may need to be raised substantially above $P_{max}$. Thus, the operating pressure for the lubes mode, is preferably substantially above $P_{cr}$ for the lubes product. The combination of operating process conditions chosen will depend upon the particular specifications of product desired.

Referring further to FIG. 2, the phase diagram shown is for the product identified herebelow, over a range of temperature and pressure ranging from about 65.5° C. (150° F.) and about 1240 kPa (180 psia), to the critical point, which is at about 282° C. (540° F.) and 5994 kPa (870 psia).

| | |
|---|---|
| $C_2^=$ | 0.03% by wt. |
| $C_3^=$ | 0.09% |
| $C_3$ | 7.6% |
| $C_4^=$ | 1.19% |
| $C_4$ | 23.14% |
| $C_5-C_9$ | 28.96% |
| $C_{10}^+$ | 38.99% |

It is evident from the phase diagram in FIG. 2 that the phase envelope has been expanded, relative to that for the feed (FIG. 1), and shifted towards higher temperatures. There is a much wider spread of temperature between the dew-point and bubble point curves at any given pressure except within about 689 kPa (100 psia) from $P_{cr}$. The difference in temperature becomes progressively smaller as the pressure increases, becoming zero at the critical point. The dewpoint curve for the product is more vertiginous than that for the feed, actually showing a convex bulge, indicating that a temperature above about 288° C. (550° F.) is favored.

Oligomerization of the feed is effected in a single zone, that is, a single fluid bed operating in the superdense phase because the heat duty of the reaction exotherm is transferred to cooling fluid flowing through coils in the reactor. The use of prior art multiple fixed beds in each of which only about a 28° C. (82° F.) exotherm may be accommodated, is avoided. The operating conditions for the fluid bed reactor to produce the foregoing product is as follows:

| | |
|---|---|
| Temperature (inlet) | 204.4° C. (400° F.) |
| WHSV | 0.3 hr |
| Pressure (inlet) | 6787 kPa (985 psia) |

There is no hydrogen introduced to the reactor, and no liquid recycle. It will be understood that the inlet temperature is typically lower than the bed temperature because the reaction exotherm raises the temperature, and heat transfer to the cooling coils in the bed is controlled to maintain the desired bed temperature.

Because the turbulent fluidization regime in our process is dictated by the exigent demands of operation at or above $P_{max}$ and $T_{max}$, this regime is readily distinguishable not only from nonturbulent dense beds and transport beds, but also from conventional dense phase turbulent fluid beds operating below $P_{max}$ and $T_{max}$. The bed density of our super-dense phase bed is in the range exceeding 500 kg/m$^3$ (31.1 lb/ft3), up to about 1500 kg/m$^3$ (93.5 lb/ft3). The preferred particle density is preferably in the range from about 1.2-2.5 g/cc. A typical super-dense fluid bed has a minimum fluidization velocity of 0.014 m/sec (0.047 ft/sec) and operates at a superficial velocity in the range from about 0.03-0.61 m/sec (0.1-2 ft/sec). The bed density and superficial velocity for operation in the distillate mode will typically be different for that in the lube mode, though both will be in the ranges stated hereinabove.

A comparable product may be produced from the same light gas feed of 57,760 lb/hr, using multiple fixed bed reactors operating under essentially similar conditions of temperature, pressure, and residence time as those in the range specified for our superdense bed. Three fixed bed reactors in series are used as described in the prior art, with progressively diminishing inlet temperatures of 254.4° C. (490° F.); 248.9° C. (480° F.); and 243.3° C. (470° F.). The first reactor inlet pressure is 6787 kPa (985 psia) and a H$_2$ circulation rate of 250 SCF/BBL and diluent rate =105,000 lb/hr. The product analysis for the multiple fixed bed is as follows:

| | |
|---|---|
| $C^=_2$ | 0.03% by wt. |
| $C_3^=$ | 0.09% |
| $C_3$ | 7.6% |
| $C_4^=$ | 1.21% |
| $C_4$ | 23.14% |
| $C_5$-$C_9$ | 30.28% |
| $C_{10}^+$ | 37.65% |

Figure 3:
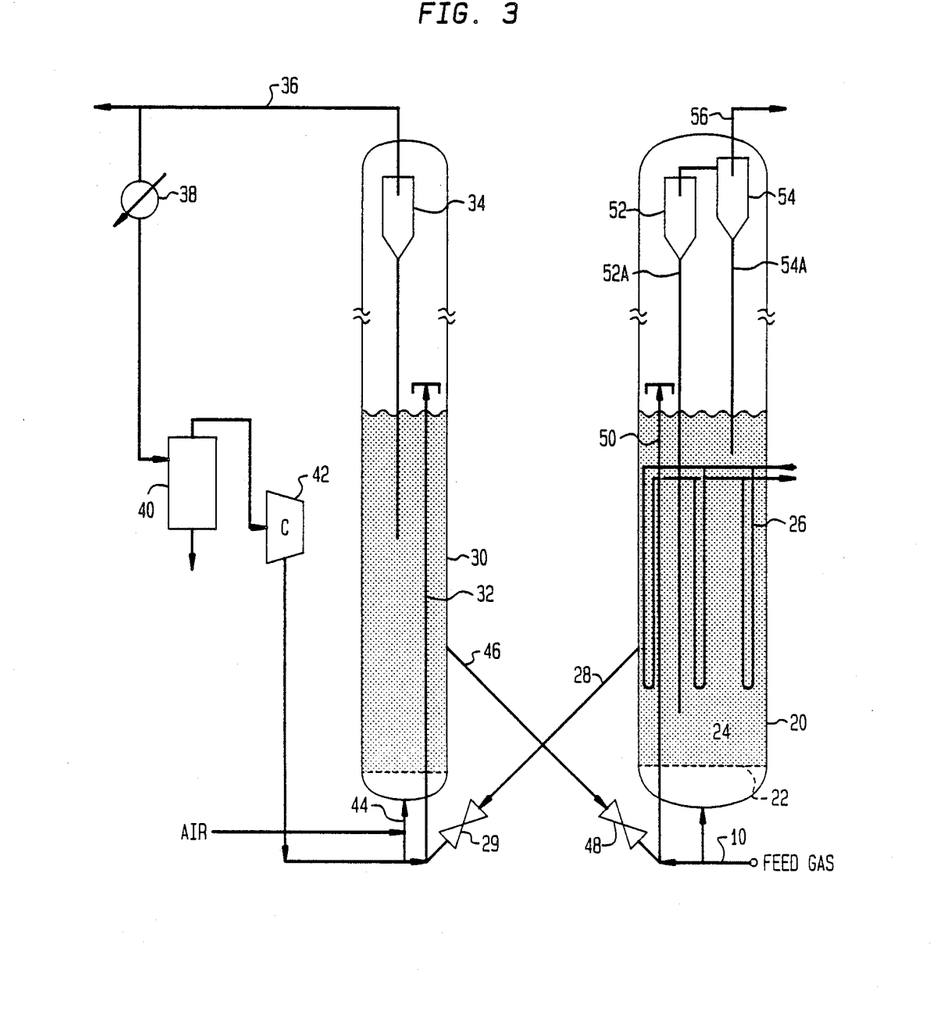
FIG. 3 is a flowsheet schematically illustrating the use of a very high pressure reactor in association with a regenerator in which coked up catalyst is oxidatively regenerated and returned to the reactor, either periodically, or continuously.

Referring now to FIG. 3, a light-gas feed rich in $C_3$-$C_4$ olefins passes, through conduit 10, into the reaction vessel 20, with the main flow being directed through the bottom inlet for distribution through grid plate 22 into the fluidization zone 24 which is at or above $P_{max}$ and $T_{max}$. Here the feed gas contacts the turbulent bed of finely divided catalyst particles. Reaction vessel 20 is shown provided with heat exchange tubes 26, which may be arranged as several separate heat exchange tube bundles so that temperature control can be separately exercised over different portions of the fluid catalyst bed. The bottoms of the tubes are spaced above feed distributor grid 22 sufficiently to be free of jet action by the charged feed through the small diameter holes in the grid. Alternatively, a substantial portion of the reaction heat can be removed by using cold feed. Baffles may be added to control radial and axial mixing. Although depicted without baffles, the vertical reaction zone can contain open end tubes above the grid for maintaining hydraulic constraints, as disclosed in U.S. Pat. No. 4,251,484 (Daviduk and Haddad). Heat released from the reaction may also be controlled by adjusting feed temperature in a known manner.

Catalyst outlet means 28 is provided for withdrawing catalyst from above bed 24 and passed for catalyst regeneration in vessel 30 via control valve 29. The partially deactivated catalyst is preferably stripped with an inert gas (steam or nitrogen) in a stripper (not shown), and oxidatively regenerated by controlled contact with air or other regeneration gas at an elevated temperature in a fluidized regeneration zone to remove carbonaceous deposits and restore acid activity. The catalyst particles are entrained in a lift gas and transported via riser tube 32 to a top portion of vessel 30. Air is distributed at the bottom of the bed to effect fluidization, with oxidation byproducts being carried out of the regeneration zone through cyclone separator 34, which returns any entrained solids to the bed. Flue gas is withdrawn via top conduit 36 for disposal; however, a portion of the flue gas may be recirculated via heat exchanger 38, separator 40, and compressor 42 for return to the vessel with fresh oxidation gas via line 44 and as lift gas for the catalyst in riser 32.

Regenerated catalyst is passed to the reaction vessel 20 through conduit 46 provided with flow control valve 48. The regenerated catalyst may be lifted to the catalyst bed with pressurized feed gas, through catalyst return riser conduit 50. Since the amount of regenerated catalyst passed to the reactor is relatively small, the temperature of the regenerated catalyst does not upset the temperature constraints of the reactor operations in significant amount. A series of sequentially connected cyclone separators 52, 54 are provided with dip legs 52A, 54A to return any entrained catalyst fines to the lower bed. These separators are positioned in an upper portion of the reactor vessel containing dispersed catalyst phase 24. Filters, such as sintered metal plate filters, can be used alone or in conjunction with cyclones.

The product effluent, separated from catalyst particles in the cyclone separating system, is then withdrawn from the reactor vessel 20 through top gas outlet means 56. The recovered hydrocarbon product comprising mainly $C_{10}^+$ olefins with some aromatics, paraffins and naphthenes is thereafter processed as required, to provide the desired distillate or lubes product.

Under optimized process conditions, the turbulent bed has a superficial vapor velocity of about 0.1 to about 0.2 (m/sec). At higher velocities, entrainment of fine particles may become excessive and beyond about 1-2 m/sec the entire bed may be transported out of the reaction zone. Lower velocities than conventionally used are preferred because in a super-dense bed, the formation of detrimental large bubbles or gas voids is not a problem. However, fine particles cannot be maintained in a superdense turbulent bed at a velocity over about 1 m/sec.

A typical preferred super-dense turbulent bed has an operating density of about 550 to 1200 kg/m$^3$, measured at the bottom of the reaction zone, becoming slightly less dense toward the top of the reaction zone, due to pressure drop and particle size differentiation. Pressure differential between two vertically spaced points in the reactor volume may be measured to obtain the average bed density at such portion of the reaction zone. For instance, in a fluidized bed system employing HZSM-5 particles having an apparent packed density of 1000 kg/m$^3$ and real density of 2430 kg/m$^3$, an average fluidized bed density of about 800 to 900 kg/m$^3$ is satisfactory.

By virtue of the turbulence experienced in the turbulent regime, gas-solid contact in the catalytic reactor is improved, providing at least 80% conversion of $C_3$–$C_6$ alkenes, enhanced selectivity, and temperature uniformity. One main advantage of this technique is the inherent control of bubble size and characteristic bubble lifetime. Bubbles of the gaseous reaction mixture are small, random and short-lived, thus resulting in such good contact between the gaseous reactants and the solid catalyst particles that typically, more than 95% of the butenes and about 99% of the propene is converted.

Despite the onus of operating under extreme pressure, the rewarding difference between our process, compared with conversion processes of the prior art, is that operation in our superdense turbulent fluidization regime can be optimized to produce distillate and lubes in exceptionally good yield even if gasoline range $C_5$–$C_9$ hydrocarbons are not recycled. The WHSV and uniform contact provides a close control of contact time between gas and solid phases, typically about 3 sec to 3 min. Another advantage of operating in the super-dense mode is the excellent control of bubble size and life span, thus avoiding large scale gas bypassing in the reactor.

As the superficial gas velocity is increased in the dense bed, eventually slugging conditions occur, and with a further increase in the superficial gas velocity, the slug flow breaks down into a turbulent regime. The transition velocity at which this turbulent regime occurs, appears to decrease with decreasing particle size. The turbulent regime extends from the transition velocity to the so-called transport velocity, as described by Avidan et al. in U.S. Pat. No. 4,547,616, incorporated herein by reference. As the transport velocity is approached, there is a sharp increase in the rate of particle carryover, and in the absence of solid recycle, the bed could empty quickly.

The MODL reactor is operable with shape selective medium pore catalysts exemplified by ZSM-5, ZSM-11, ZSM-12, ZSM-23, ZSM-35, ZSM-38, ZSM-48 and other similar materials. U.S. Pat. No. 3,702,886 describing and claiming ZSM-5; U.S. Reissue Pat. No. Re. 29,948 describing and claiming a crystalline material with an X-ray diffraction pattern of ZSM-5; and, U.S. Pat. No. 4,061,724 describing a high silica ZSM-5 referred to as "silicalite" are each incorporated by reference thereto as if fully set forth herein. Similarly, the disclosures relating to ZSM-11, ZSM-12, ZSM-23, ZSM-35, ZSM-38, and ZSM-48 set forth in U.S. Pat. Nos. 3,709,979, 3,832,449, 4,076,842, 4,016,245, 4,046,859, and 4,375,573, respectively, are each incorporated by reference thereto as if fully set forth herein.

In general the aluminosilicate zeolites are most effectively employed in our MODL reactor. However, zeolites in which some other framework element which is isoelectronic to aluminum and which is present in partial or total substitution of aluminum can be advantageous. Illustrative of elements which can be substituted for part or all of the framework aluminum are boron, gallium, titanium, and, in general, any trivalent metal which is heavier than aluminum. Specific examples of such catalysts include ZSM-5 and zeolite Beta containing boron, gallium and/or titanium. In lieu of, or in addition to, being incorporated into the zeolite framework, these and other catalytically active elements can also be deposited upon the zeolite by any suitable procedure, e.g., by impregnation.

The aluminosilicates are preferred catalysts. These can be described as a three-dimensional framework of $SiO_4$ and $AlO_4$ tetrahedra in which the tetrahedra are cross-linked by the sharing of oxygen atoms whereby the ratio of total aluminum and silicon atoms to oxygen atoms is 1:2. In their hydrated form, the aluminosilicates may be represented by the formula:

$$M_{2/n}O:Al_2O_3:wSiO_2:YH_2O$$

wherein M represents at least one cation which balances the electrovalence of the tetrahedra, n represents the valence of the cation, w the moles of $SiO_2O$ and Y the moles of $H_2$. The cations can be any or more of a number of metal ions, depending upon whether the aluminosilicate is synthesized or occurs naturally. Typical cations include sodium, lithium, potassium, silver, magnesium, calcium, zinc, barium, iron, nickel, cobalt and manganese. Although the proportions of inorganic oxides in the silicates and their spatial arrangements may vary affecting distinct properties in the aluminosilicate, the main characteristic of these materials is their ability to undergo dehydration without substantially affecting the $SiO_4$ and $AlO_4$ framework.

Aluminosilicates falling within the above formula are well known and, as noted, include synthesized aluminosilicates, natural aluminosilicates, and certain caustic treated clays. Among the aluminosilicates are included zeolites, Y, L, S, X, levynite, erionite, faujasite, analcite, paulingite, noselite, phillipsite, datolite, gmelinite leucite, scapolite, mordenite as well as certain caustic treated clays such as montmorillonite and kaolin families. The preferred aluminosilicates are those having pore diameters of greater than about 6 Å (Angstroms).

Aluminosilicates may be treated with a fluid medium or media in a known manner to include a wide variety of aluminosilicates both natural and synthetic which have a crystalline, or, combination of crystalline and amorphous structure. These "promoters" may be provided in the catalyst by impregnation or ion exchange.

Though the process of the invention is operable with any of the aluminosilicates the preferred catalyst is a group of medium pore siliceous materials having similar pore geometry. Most prominent among these intermediate pore size zeolites is ZSM-5, which is usually synthesized with Bronsted acid active sites by incorporating a tetrahedrally coordinated metal, such as Al, Ga, B or Fe, within the zeolitic framework. These medium pore zeolites are favored for acid catalysis; however, the advantages of ZSM-5 type structures may be utilized by employing highly siliceous materials or crystalline metallosilicate having one or more tetrahedral species having varying degrees of acidity. The ZSM-5 crystalline structure is readily recognized by its X-ray diffraction pattern, which is described in U.S. Pat. No. 3,702,866 (Argauer, et al.), incorporated by reference herein.

The oligomerization catalysts preferred for use herein include the medium pore (i.e., about 5–7 Å) shape-selective crystalline aluminosilicate zeolites having a silica-to-alumina ratio of at least 12, a constraint index of about 1 to 12, preferred alpha during operation in the range from about 5 to about 15, and acid cracking activity of about 10–250. In the MODL reactor the coked catalyst may have an apparent activity (alpha value) of about 2 to 25 under the process conditions to achieve the required selectivity and per pass conversion. Representative of the ZSM-5 type zeolites are ZSM-5, ZSM-11, ZSM-12, ZSM-22, ZSM-23, ZSM-35 and ZSM-38. Details about ZSM-5 are disclosed in U.S. Pat. No. 3,702,886 and U.S. Pat. No. Re. 29,948. Other suitable zeolites are disclosed in U.S. Pat. Nos. 3,709,979; 3,832,449; 4,076,979; 3,832,449; 4,076,842; 4,016,245; 4,046,839; 4,414,423; 4,417,086; 4,517,396 and 4,542,251, the disclosures of which are incorporated by reference thereto as if fully set forth herein. A typical zeolite catalyst component having Bronsted acid sites may consist essentially of aluminosilicate ZSM-5 zeolite with 5 to 95 wt. % silica and/or alumina binder.

These siliceous zeolites may be employed in their acid forms, ion exchanged, or impregnated with one or more suitable metals, such as Ga, Pd, Zn, Ni, Co and/or other metals of Periodic Groups III to VIII. The zeolite may include a hydrogenation-dehydrogenation component (sometimes referred to as a hydrogenation component) which is generally one or more metals of group IB, IIB, IIIB, VA, VIA or VIIIA of the Periodic Table (IUPAC), especially aromatization metals, such as Ga, Pd, etc. Useful hydrogenation components include the noble metals of Group VIIIA, especially platinum, but other noble metals, such as palladium, gold, silver, rhenium or rhodium, may also be used. Base metal hydrogenation components may also be used, especially nickel, cobalt, molybdenum, tungsten, copper or zinc. The catalyst materials may include two or more catalytic components, such as a metallic oligomerization component (e.g., ionic $Ni^{+2}$, and a shape-selective medium pore acidic oligomerization catalyst, such as ZSM-5 zeolite) which components may be present in admixture or combined in a unitary bifunctional solid particle. It is possible to utilize an ethene dimerization metal or oligomerization agent to effectively convert feedstock ethene in a continuous reaction zone.

Certain of the ZSM-5 type medium pore shape selective catalysts are sometimes known as pentasils. In addition to the preferred aluminosilicates, the borosilicate, ferrosilicate and "silicalite" materials may be employed. It is advantageous to employ a standard ZSM-5, suitably modified, having a silica:alumina molar ratio in the range from 12:1 to 100:1, a constraint index in the range from 5 to 12, and with the aforesaid alpha value to convert substantially all the olefins in the feedstock.

ZSM-5 type pentasil zeolites are particularly useful in the process because of their regenerability, long life and stability under the extreme conditions of operation. Usually the zeolite crystals have a crystal size from about 0.01 to over 2 microns or more, with 0.02–1 micron being preferred, and an apparent crystal density in the range from about 0.6 to 1.9 $gm/cm^3$ In order to obtain the desired particle size for fluidization in the turbulent regime, the zeolite catalyst crystals are bound with a suitable inorganic oxide, such as silica, alumina, etc. to provide a zeolite concentration of about 5 to 95 wt. %. In the description of preferred embodiments a 25% HZSM-5 catalyst contained within a silica-alumina matrix and having a fresh alpha value of about 80 is employed unless otherwise stated.

Operation of a super-dense phase turbulent regime is also distinguishable over a prior art dense phase turbulent regime in that the particle size distribution to achieve overall homogeneity requires a smaller percentage of "fines". The super-dense phase regime uses only from 5% to 20% by wt of fines. It is advantageous to employ a particle size range consisting essentially of 1 to 200 microns. Average particle size is usually about 20 to 150 microns, preferably 50 to 100 microns. The optimum particle size distribution is obtained with a mixture of larger and smaller particles within the above-specified range, having from 5–20% by weight fines. Close control of distribution is maintained with the fines in the size range less than 32 microns.

The average particle density of the catalyst as used may be tailored for optimum fluid-bed operation by compositing it with a matrix component of appropriate density. Such matrix components which provide particles of progressively increasing overall packed density are silica, alumina, beryllia, magnesia, barium oxide, zirconia, and titania, yielding values of from about 2.2 $gm/cm^3$ for silica, up to about 5.9 $gm/cm^3$ for zirconia. In our MODL reactor, the overall packed density of medium pore zeolite particles so composited, including the matrix component, can advantageously vary from about 0.6 to about 4 $gm/cm^3$, more preferably from about 2 to about 3 $gm/cm^3$.

Several useful parameters contribute to fluidization in the turbulent regime in accordance with the process of the present invention. When employing a ZSM-5 type zeolite catalyst in fine powder form such a catalyst should comprise the zeolite suitably bound or impregnated on a suitable support with a solid density (weight of a representative individual particle divided by its apparent "outside" volume) in the range from 0.6–2 g/cc, preferably 0.9–1.6 g/cc. When these solid particles are placed in a fluidized bed where the superficial fluid velocity is 0.06–0.5 m/s, operation in the turbulent regime is obtained. Those skilled in the art will appreciate that at higher pressures in the range, a lower gas velocity may be employed to ensure operation in the turbulent fluidization regime.

The MODL reactor is designed as a high-pressure vessel required to contain a turbulent fluid-bed operating to produce optimum yields of the desired oligomers, and important criteria are taken into consideration. The bed of catalyst in the reactor is desirably in the range from about 3–20 meters in height, preferably about 8 meters, and, operates at relatively low WHSV, preferably less than 10 $hr^{-1}$. Fine particles may be included in the bed, especially due to attrition, and the fines may be entrained in the product gas stream. A typical turbulent bed may have a catalyst carryover rate of about 1.5 times the reaction zone inventory per hour. If the fraction of fines becomes large, a portion of the carryover may be removed from the system and replaced by larger particles. It is desirable to have a fine particle separator such as a cyclone and/or filter means, disposed within or outside the reactor shell to recover catalyst carryover and return this fraction continuously to the bottom of the reaction zone for recirculation at a rate of about one catalyst inventory per hour. Optionally, fine particles carried from the reactor vessel entrained with effluent gas can be recovered by a sintered metal filter operating at the MODL reactor conditions.

Typically, in carrying out the process in the very high pressure MODL reactor, the light gas feed is brought into contact with a medium pore zeolite catalyst having a silica to alumina ratio in the range from 12 to about 1000, more preferably from 50 to 90, maintained as a super-dense phase in a fluid-bed at or above $P_{max}$ and $T_{max}$, but excluding critical conditions, at a temperature at which no liquid will form in the bed, while the light gas is flowed through the reactor at a superficial vapor velocity in the range from about 0.031 m/sec (0.1 ft/sec) to about 0.616 m/sec (2 ft/sec), preferably from 0.031 m/sec (0.1 ft/sec) to 0.308 m/sec (1 ft/sec). Most preferred superficial velocity is in the range from about 0.1 m/sec (0.3 ft/sec) to about 0.3 m/sec with a HZSM-5 catalyst having a constraint index in the range from 5-12, and, an apparent alpha in the range from about 5 to about 15, operating with a WHSV (based on olefin equivalent and total reactor catalyst inventory) in the range from about 0.1 to 5 $hr^{-1}$.

The operation of the turbulent fluid bed in the super-dense phase produces a remarkably low coking rate, generally less than 0.05 wt % of the olefins in the feed, which low rate allows one to operate the bed without regeneration for a long period of time. In some instances periodic regeneration may be a preferred mode of operation. If not continuously regenerated, the coke content will gradually increase to about 15% by wt of the catalyst, at which point the run is desirably terminated.

When continuous regeneration is chosen, the regenerator will be operated at the highest pressure at which effective decoking can be quickly effected without exceeding a temperature deleterious to the activity of the regenerated catalyst. Typically, the regeneration pressure is in the same range as that for the reactor. Whether withdrawal of coked-up catalyst is periodic or continuous, the desired activity of the regenerated catalyst is to be maintained.

The activity of the catalyst at or above $P_{max}$ and $T_{max}$ is a distinguishing characteristic of our process. This activity is evidenced by a per pass conversion of lower olefins of at least 80%, typically better than 90%, and a selectivity to $C_5+$ hydrocarbons of at least 80%. Though $C_{10}^-$ hydrocarbons in the product are not particularly desirable, under certain operating conditions, a relatively large amount of gasoline range hydrocarbons, up to about an equal amount by weight of distillate, may be made during operation in the distillate mode. Typically, the ratio of distillate to gasoline range hydrocarbons is 5:1, and may be as much as 20:1.

Operating conditions of our process in the lube mode are deliberately tailored to produce $C_{20}+$ oligomers though, under particular process conditions, as much as about an equal amount weight of about $C_{22}^-$ oligomers (non-lubes) which mainly constitute distillate, may be produced during operation. Typically, the ratio of lubes to non-lubes is 2:1, and may be as much as 20:1.

Yet another distinguishing characteristic of our process is that, despite the stringent operating conditions, the lower $C_2-C_4$ alkanes in the feed are substantially unconverted, that is, there is no net depletion of alkanes. This can be accounted for by the formation of some $C_2-C_4$ alkanes with a purely $C_3-C_5$ olefin feed.

To maintain the high per pass conversion and selectivity in the super-dense bed, the catalyst is preferably continuously regenerated. Whether regeneration is periodic or continuous, it is done by withdrawing a portion of coked catalyst from the reaction zone, oxidatively regenerating the withdrawn catalyst and returning regenerated catalyst to the reaction zone at a rate sufficient to maintain the desired selectivity and per pass conversion, each at least 80%, based on the total olefins in the feedstream.

It will be appreciated that the design, construction and operating conditions of a commercial oligomerization reaction vessel will be dictated by the economics of producing either distillate or lubes, and the optimum operating conditions will be dictated by the conversions sought. Such a reactor will have a height to diameter ratio of at least 5, a pressure rating of at least 14000 kPa, and a temperature rating of at least 380° C. The feed to the reactor will preferably be preheated by the internal coils 26 through which liquid feed is pumped under sufficient pressure to provide a non-liquid feed to the fluid bed, and at a temperature not much lower than about 20° C. from the desired operating temperature in the fluid bed. The regenerator will typically operate in the range from about 371° C.–510° C. (700° F.–950° F.), and the flue gas from the regeneration zone will be cooled to a sufficiently low temperature in the range from about 35° C.–50° C. (95° F.–510° F.), so that a portion of it may be recycled to the regeneration zone, and the remainder discharged.

In the best mode for the production of distillate range hydrocarbons from a light olefinic feedstock having a major proportion by wt of $C_3-C_6$ alkenes, the oligomerized product will contain less than about 60% by wt of ($C_{10}^-$) hydrocarbons, and about 40% by wt, or more, of ($C_{10}^+$) hydrocarbons. In most instances, a major portion of the ($C_{10}^-$) hydrocarbons are separated from the product stream and recycled to the super-dense reaction zone.

EXAMPLE

In this illustrative example, the process is carried out in a very high pressure reactor in which a light gas having a predominant amount by weight of monomeric lower $C_3-C_6$ olefins is brought into contact with a medium pore HZSM-5 zeolite catalyst having a silica to alumina ratio of about 70. The HZSM-5 catalyst has a constraint index of about 10; and, an alpha of about 10. The catalyst is maintained as a super-dense phase in a fluid-bed at supercritical conditions at a pressure of 6787 kPa (985 psia) and, with the inlet temperature of the feed being 254.4° C. (490° F.), the temperature of the bed is maintained at 315.5° C. (600° F.). The light gas is flowed through the reactor at a WHSV of 0.3 $hr^{-1}$, operating in the distillate mode, and the results are for a single pass, that is, without any recycle of $C_5-C_9$ gasoline range hydrocarbons.

For comparison, the same feed is flowed through a series of fixed bed reactors operating at substantially the same inlet pressure of 985 psia, and at temperatures of 254.4° C., 248.9° C., and, 243.3° C., and a diluent rate (assumed inert) of 105,500 lb/hr.

The runs are presented side-by-side in Table I below.

TABLE I

| | lb/hr, based on fresh feed | | |
|---|---|---|---|
| Fresh Feed | | Product | |
| Light Gas (FCC LPG) H$_2$ circ.rate | | Fluid Bed | Fixed Bed 250 SCF/BBL |
| C$_2$= | — | 20 | 20 |
| C$_3$= | 14,370 | 60 | 60 |
| C$_3$ | 4,410 | 4,410 | 4,410 |
| C$_4$= | 25,250 | 690 | 700 |
| C$_4$ | 13,370 | 13,370 | 13,370 |
| C$_5$–C$_9$ | — | 16,730 | 17,490 |
| C$_{10}$+ | — | 22,480 | 21,710 |
| Total | 57,760 | 57,760 | 57,760 |

As is evident from the foregoing example, the total olefins in the feedstream was 39,980 lb/hr; the combined C$_3$–C$_4$ olefins in the product was 750 lb/hr; so that the per pass conversion is better than 95%. Typically, the per pass conversion is over 90%, though in some cases where the olefin content is relatively low, the per pass conversion may be less.

Having thus provided a general discussion, and a specific illustration of the best mode of operation of a single zone super-dense phase turbulent bed, and described the oligomerization of a predominantly monomeric olefinic light gas feedstream in such a bed, it is to be understood that no undue restrictions are to be imposed by reason thereof except as provided by the following claims.

We claim:

1. A catalytic process for upgrading a C$_2$+ olefin feedstream to a heavier product stream rich in C$_{10}$+ aliphatic hydrocarbons, said process comprising,
    (a) contacting said olefin feedstream with a finely divided medium pore zeolite metallosilicate catalyst having a silica:alumina ratio greater than 12, and a constraint index in the range from about 1 to about 12, maintained as a super-dense fluid-bed operating in a single zone turbulent regime at or above a pressure P$_{max}$ and a temperature T$_{max}$ at which there be no liquid phase present,
    (b) flowing said olefin feedstream through said bed at a weight hourly space velocity (WHSV) in the range from about 0.05 to about 50 hr$^{-1}$, without forming a liquid phase in said bed,
    (c) maintaining a catalyst fines content of from about 5% to about 20% by wt, based on the weight of the catalyst in the bed, said fines having a particle size less than 32 microns, and,
    (d) recovering said C$_{10}$+ aliphatic hyrdocarbons from said product stream leaving said bed at or above said P$_{max}$ and T$_{max}$.

2. The process of claim 1 wherein said olefin feedstream consists essentially of C$_2$–C$_6$ monoolefins, and, said P$_{max}$ and T$_{max}$ lie outside a pressure and temperature region circumscribed by an arc having a radius corresponding to about a 344.5 kPa (50 psi) differential from the critical pressure and temperature point P$_{cr}$, T$_{cr}$, of hydrocarbons present as a mixture in said bed, said region being bounded by that portion of the bubble-point/dewpoint curve which is downwardly inclined from said point.

3. The process of claim 2 wherein said bed operates at a bed density, measured at the bottom of the reaction zone, greater than 500 kg/m$^3$, a temperature in the range from about 204° C. (400° F.) to about 371° C. (700° F.), and a pressure in the range from about 2857 kPa (400 psig) to about 13880 kPa (2000 psig).

4. The process of claim 3 wherein said catalyst is a medium pore size siliceous metallosilicate acid zeolite having a constraint index in the range from 5 to about 12, an alpha in the range from 2 to about 100, and said silica:alumina ratio is in the range from about 12:1 to 70:1.

5. The process of claim 4 wherein said C$_2$–C$_6$ monoolefins comprise a major proportion by weight of propene and butenes.

6. The process of claim 4 wherein said fluid bed is maintained in a reactor operated in a distillate mode at relatively low pressure in the range from about 2857 kPa to about 10436 kPa (400 psig–1500 psig), and relatively high temperature in the range from 260° C. to about 371° C. (500° F.–700° F.); and, said heavies consist essentially of distillate having a boiling in the range from about 138° C. to about 349° C. (280° F. –660° F.)

7. The process of claim 4 wherein said fluid bed is maintained in a reactor operated in a lubes mode at relatively high pressure in the range from about 5270 kPa to about 13881 kPa (500 psig 2000 psig), and relatively low temperature in the range from 204° C. to about 315° C. (400° F. –600° F.); and, said heavies consist essentially of lubes having a viscosity in the range from 10 cp to about 100 cp, measured at 100° C.

8. The process of claim 4 wherein said monoolefin feedstream is essentially free of hydrogen.

9. A process for oligomerizing a "light gas" feedstream containing C$_2$–C$_6$ lower olefins and diluent C$_2$–C$_6$ paraffins, to C$_{10}$+ "heavies", comprising,
    (a) operating a super-dense phase fluid bed of a finely divided medium pore zeolite metallosilicate catalyst having a silica:alumina ratio greater than 12, and a constraint index in the range from about 1 to about 12, at or above a temperature T$_{max}$ and a pressure P$_{max}$ at which no liquid may form, said P$_{max}$ and T$_{max}$ lying outside a pressure and temperature region circumscribed by an arc having a radius corresponding to about a 344.5 kPa (50 psi) differential from the critical pressure and temperature point P$_{cr}$, T$_{cr}$, of hydrocarbons present as a mixture in said bed, said region being bounded by a portion of the bubble-point/dewpoint curve which is downwardly inclined from said point; and,
    (b) recovering a product stream in which said C$_{10}$+ heavies (having more than 10 carbon atoms) are present in a major amount by weight relative to that of monomeric lower olefins.

10. The process of claim 9 wherein said reaction pressure is in the range from about 2857 kPa (400 psig) to about 13880 kPa (2000 psig), and said reaction temperature is in the range from about 204° C. to 371° C. (400° F. to about 700° F.).

11. The process of claim 10 wherein said catalyst is a medium pore size siliceous metallosilicate acid zeolite having a constraint index in the range from 5 to about 12, an alpha in the range from 3 to about 100, and a silica:alumina ratio in the range from about 12:1 to 70:1.

12. A fluidized bed catalytic process for converting an olefinic light gas feedstock comprising a major portion by weight of monomeric C$_3$–C$_6$ alkenes to oligomerized hydrocarbons rich in aliphatics and aromatics having at least ten carbon atoms (C$_{10}$+), comprising the steps of
    maintaining a super-dense turbulent fluidized bed in a reactor operating at a pressure in the range from about 2857 kPa to about 13880 kPa, and temperature of about 204° C. to about 399° C., under conditions at which no liquid phase is present, said catalyst being a particulate zeolite having a silica:alumina molar ratio in the range from about 12:1 to 70:1, an apparent zeolite crystal density in the range from about 0.9 to 1.6 g/cm$^3$, an operating alpha in the range from 5 to about 25, an average catalyst density particle size of about 20 to 200 microns containing about 5 to 20 weight percent of fine particles having a particle size of less than 32 microns, and an overall packed density in the range from about 0.6 to 4 gm/cm$^3$ for particles composited with a matrix component;

passing said feedstock upwardly through said superdense fluidized bed in a single pass under turbulent flow conditions which provide reaction severity conditions sufficient to convert at least 80% by weight of said $C_3$–$C_6$ alkenes to $C_{10}{}^+$ hydrocarbons;

maintaining turbulent fluidized bed conditions at a superficial feedstock velocity of about 0.02 to 0.6 m/sec (meters per second) through said bed having an average fluidized bed density, measured at the bottom of the reaction zone, in the range exceeding 500 kg/m$^3$, up to about 1500 kg/m$^3$; and, recovering hydrocarbon product containing a major amount by weight of said oligomerized hydrocarbons.

13. The process of claim 12 wherein the catalyst comprises a siliceous metallosilicate acid zeolite selected from the group consisting of ZSM-5, ZSM-11, ZSM-12, ZSM-23, ZSM-35, ZSM-38, and ZSM-48, having a constraint index in the range from 1 to about 12, an alpha in the range from 5 to about 100, and a silica:alumina ratio in the range from about 20:1 to 70:1.

14. The process of claim 13 wherein said olefinic content of said feedstock consists essentially of at least 20% by wt of propylene and heavier olefins ($C_4{=}+$), and said turbulent bed has a fluidized height of at least 3 meters.

15. The process of claim 13, including in addition, the steps of separating hydrocarbons having less than about 22 carbon atoms ($C_{22}{}^-$) from said hydrocarbon product, and, recycling said ($C_{22}{}^-$) hydrocarbons to said reactor.

16. In a process for continuously converting an olefinic light gas feedstock comprising a major portion by weight of $C_3$–$C_6$ alkenes to hydrocarbons rich in aliphatics and aromatics having least ten carbon atoms ($C_{10}{}^+$) wherein said feedstock is contacted with a fluidized bed of medium pore zeolite catalyst under conversion conditions, the improvement which comprises, maintaining said fluidized catalyst bed as a superdense bed in a vertical reactor column having a turbulent reaction zone of catalyst having a constraint index in the range from 1 to about 12, an alpha in the range from 5 to about 100, and a silica:alumina ratio in the range from about 20:1 to 70:1, with an average density measured at the bottom of the reaction zone, exceeding 500 kg/m$^3$, up to about 1500 kg/m$^3$, at a pressure in the range from 2857 kPa to 13880 kPa and a temperature in the range from about 204° C. to about 371° C. at or above conditions of maximum pressure $P_{max}$ and temperature $T_{max}$ under which conditions no liquid phase may be present, by passing said feedstock containing at least 20% by weight of propylene and a total $C_3$–$C_6$ alkene content of about 30 to 80 wt %, upwardly through the reaction zone while maintaining a superficial velocity greater than that at which slug flow breaks down but less than transport velocity for the average catalyst particle having an overall packed density of about 2.2 gm/cm$^3$; and, withdrawing a portion of coked catalyst from the reaction zone, oxidatively regenerating the withdrawn catalyst and returning regenerated catalyst to the reaction zone at a rate sufficient to maintain a selectivity to $C_5{}^+$ hydrocarbons of at least 80%, and a per pass conversion of at least 80% of said $C_3$–$C_6$ alkenes in said feedstock.

17. The process of claim 16 wherein the superficial vapor velocity of said light gas feedstock is in the range from about 0.1 m/sec to about 0.2 m/sec; the weight hourly space velocity is in the range from about 0.1 to 5 hr$^{-1}$; said catalyst has a constraint index in the range from 5 to about 12, an alpha in the range from 5 to about 15; and, the $C_3$–$C_6$ alkane:alkene weight ratio in said feedstock is in the range from about 0.02:1 to 5:1.

18. The process of claim 17 wherein said reactor operates in a distillate mode, the pressure in said bed is maintained in the range from about 2857 kPa to about 10436 kPa (400 psig - 1500 psig), and the temperature in the range from 260° C. to about 371° C. (500° F. -700° F.), to form a product consisting essentially of ($C_{10}+$) hydrocarbons including distillate boiling in the range from about 138° C. to about 349° C. (280° F. -660° F.).

19. The process of claim 17 wherein said reactor operates in a lubes mode, the pressure in said bed is maintained in the range from about 5270 kPa to about 13881 kPa (500 psig -2000 psig), and the temperature in the range from 204° C. to about 315° C. (400° F. -600° F.), to form a product consisting essentially of ($C_{22}+$) hydrocarbons including lubes having a viscosity in the range from 10 cp to about 100 cp, measured at 100° C.

20. The process of claim 18 including, in addition, separating from said product a predetermined $C_{10}{}^-$ hydrocarbons portion having a boiling point lower than that of said distillate to provide a $C_{10}{}^-$ recycle stream, and recycling said $C_{10}{}^-$ stream to said bed to maximize production of said distillate in said reactor.

21. The process of claim 19 including, in addition, separating from said product a predetermined $C_{22}{}^-$ hydrocarbons portion having a boiling point lower than that of said lubes to provide a $C_{22}{}^{31}$ recycle stream, and recycling said $C_{22}{}^-$ stream to said bed maximize production of said lubes in said reactor.

22. The process of claim 18 wherein the ratio of $C_{10}{}^+$ distillate to $C_5$–$C_9$ gasoline is greater than 1:1; and, the ratio of $C_{20}$ lubes to $C_{10}{}^+$ distillate is greater than 1:1.

* * * * *

UNITED STATES PATENT AND TRADEMARK OFFICE
CERTIFICATE OF CORRECTION

PATENT NO. : 4,877,921

DATED : October 31, 1989

INVENTOR(S) : Mohsen N. Harandi and Hartly Owen

It is certified that error appears in the above-identified patent and that said Letters Patent is hereby corrected as shown below:

Col 9, line 34, "31.1 lb/ft3" should be 31.1 lb/ft$^3$

Col 18, line 3, Delete "having"

Col 18, line 36, Delete "liquid may form" should be --liquids are formed--.

Signed and Sealed this

Twelfth Day of February, 1991

*Attest:*

HARRY F. MANBECK, JR.

*Attesting Officer*    *Commissioner of Patents and Trademarks*